(12) United States Patent
Chen et al.

(10) Patent No.: US 6,399,850 B1
(45) Date of Patent: Jun. 4, 2002

(54) ALDEHYDE NEUTRALIZER

(75) Inventors: Xiaolan Chen, Irvine; Charles G. Roberts, Long Beach, both of CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/321,964

(22) Filed: May 28, 1999

(51) Int. Cl.[7] .................................. A62D 3/00
(52) U.S. Cl. ........................ 588/205; 210/749
(58) Field of Search .................. 588/205; 210/749, 210/908

(56) References Cited

FOREIGN PATENT DOCUMENTS

JP 7-204661 * 8/1995

OTHER PUBLICATIONS

Seyhan Ege, Organic Chemistry, 1994, p. 534–535.*

H. Y. Cheung, M. R. W. Brown, "Evaluation of glycine as an inactivator of glutaraldehyde," 34 J. Pharm. 211 (1982).

* cited by examiner

Primary Examiner—Steven P. Griffin
Assistant Examiner—Eileen E. Nave
(74) Attorney, Agent, or Firm—Blakely, Sokoloff, Taylor & Zafman

(57) ABSTRACT

Methods and a system of using amino acids are disclosed as being useful in neutralizing aldehydes in waste. These neutralizers allow waste containing aldehyde to be more safely and cheaply disposed.

18 Claims, 2 Drawing Sheets

ALDEHYDE NEUTRALIZER

BACKGROUND OF THE INVENTION

1. Field of the Invention

The invention relates to neutralization of aldehyde for the purpose of complying with waste disposal requirements established by federal and state environmental protection agencies.

2. Description of Related Art

Waste disposal of aldehydes has become increasingly more difficult over the years. Treatment of wastes containing a certain amount of aldehyde prior to placement of the waste into the environment is required by law. The extent of such treatment may vary depending upon the location of where the waste is generated and the stringency of the environmental standards in that area. For example, waste containing aldehyde may be classified as a hazardous waste in California under 22 CAL. CODE REGS., TIT. 22, §66696. Formaldehyde also may be considered a hazardous waste on the federal level under 40 C.F.R. §261.33(e) if it is a commercial chemical product (e.g., pure technical grade formaldehyde or formaldehyde is the sole active ingredient of the product that is to be disposed). Every state has an environmental regulation that is at least as stringent as this formaldehyde standard. State regulations also may be more stringent than this standard.

Additionally, facilities that discharge waste water to Publicly Owned Treatment Works ("POTW") or directly into navigable waters may be required to meet standards that are established by a government agency. The standard may vary for each facility depending upon the quality of the receiving water and the concentration of aldehyde found in the waste water that is discharged into the environment by industry in that area.

Waste containing aldehyde may be generated by a variety of processes. For example, aldehydes such as gluteraldehyde and ortho-phthalaldehyde ("OPA") are used in disinfecting medical devices or instruments. Waste containing aldehydes also may be generated by painting operations, stripping operations related to floors, or other manufacturing operations.

Typically, ammonia and sodium bisulfite ("SBS") are used to treat many aldehydes. These compounds, however, have not proven to be effective at neutralizing OPA in accordance with environmental regulations.

A waste is classified as a hazardous waste in California if the waste being examined "has an acute aquatic 96-hour $LC_{50}$ less than 500 milligrams per liter (mg/L) when measured in soft water (total hardness 40 to 48 milligrams per liter of calcium carbonate) with fathead minnows . . . " 22 CAL. CODE REGS., TIT. 22, §66696. $LC_{50}$ represents the concentration of a waste that is necessary to kill 50% of a particular animal exposed to a waste.

Note that a nonhazardous waste is generally considered by federal and state environmental agencies as a waste that does not satisfy the criteria set forth in defining a hazardous waste. Therefore, wastes generated in California that have a $LC_{50}$>500 mg/L are nonhazardous wastes and wastes having $LC_{50}$<500 mg/L are classified as hazardous. SBS, for example, in combination with OPA, produces a product that is generally considered hazardous under California environmental law as shown in Table 1 by $LC_{50}$ being consistently below 500 mg/L. For this study, CIDEX® OPA (commercially available from Advanced Sterilization Products®, a Johnson & Johnson Company of Irvine, Calif.) was used to supply the OPA.

TABLE 1

Neutralization Of OPA using SBS

| Sample Type | OPA Content % | $LC_{50}$ (mg/l) | Comments |
| --- | --- | --- | --- |
| Fresh CIDEX ® OPA at 0.3% OPA | 0.301% | 31.1 mg/l | 1 |
| Fresh CIDEX ® OPA at 0.15% OPA | 0.158% | 50.4 mg/l | 2 |
| Reuse CIDEX ® OPA at 0.3% OPA | 0.295% | 31.1 mg/l | 3 |
| SBS/OPA = 4:1 | N/A | 68.3 mg/l | 4 |
| SBS/OPA = 2:1 | N/A | 46.3 mg/l | 5 |

1. Fresh CIDEX ® OPA at 0.3% OPA was prepared by diluting the fresh Cidex OPA solution with deionized water.
2. Fresh CIDEX ® OPA at 0.15% OPA was prepared by diluting the fresh Cidex OPA solution with deionized water to the level of 0.15% of OPA.
3. Reuse of CIDEX ® OPA at 0.3% OPA was prepared by diluting the simulated reuse CIDEX ® OPA (14 days) with deionized water.
4. SBS/OPA = 4:1, 10% SBS (10 ml) was combined with 100 ml of the fresh CIDEX ® OPA solution at 0.3% OPA (sample 1 above) at the SBS/OPA molar ratio of 4 to 1 for 30 minutes, and then the combined solution was used in the 22 CAL. CODE REGS., TIT. 22, § 66696 test for California.
5. SBS/OPA = 2:1, 10% SBS (5 ml) was combined with or 100 ml of the fresh CIDEX ® OPA solution at 0.3% OPA (sample 1 above)at the SBS/OPA molar ratio of 2 to 1 for 30 minutes, and then the combined solution was used for the fish test in the 22 CAL. CODE REGS., TIT. 22, § 66696 test for California.

In addition to lacking the ability to effectively neutralize OPA, ammonia and SBS are problematic since they may be harmful to the environment.

FIG. 1 shows that when OPA is combined with SBS at the molar ratio of SBS/OPA=4:0 for 30 minutes, OPA has been neutralized since the OPA concentration is nondetectable in a high performance liquid chromatography (HPLC) analysis method, which has detection limit for OPA at 10 ppm. However, the end-product is still classified as a hazardous waste as shown in Table 1. Therefore, even though the aldehyde is neutralized completely by a neutralizer, the end-product may still be a hazardous waste.

Although glycine has been shown to neutralize gluteraldehyde (see H. Y. Cheung & M. R. W. Brown, Evaluation of Glycine As An Inactivator of Gluteraldehyde, 34 J. PHARM. 211 (1982)), the toxicity of reaction products of glycine has not been studied. Therefore, it is not known from this article whether the reaction product is nonhazardous. Accordingly, it is desirable to have a neutralizer that effectively neutralizes aldehydes in compliance with environmental standards and is less toxic to the environment.

SUMMARY OF THE INVENTION

A method and system for neutralizing aldehydes to form a nonhazardous product is disclosed. In one aspect, the invention provides a generally nonhazardous means for neutralizing aldehydes in accordance with applicable environmental regulations prior to disposal. Additionally, the neutralization is more effective and cost efficient than traditional chemical treatment methods of aldehydes.

In one embodiment, the neutralization method comprises combining an amino acid in solution or in solid form to a contained solution (or solid form) comprising an aldehyde to form an addition product and then combining the addition product for a predetermined time to yield a nonhazardous product. A system for neutralizing an aldehyde is also disclosed.

Additional features, embodiments, and benefits will be evident in view of the figures and detailed description presented below.

BRIEF DESCRIPTION OF THE DRAWINGS

The features, aspects, and advantages of the invention will become more thoroughly apparent from the following detailed description, appended claims, and accompanying drawings in which:

DETAILED DESCRIPTION OF THE INVENTION

Figure 1:
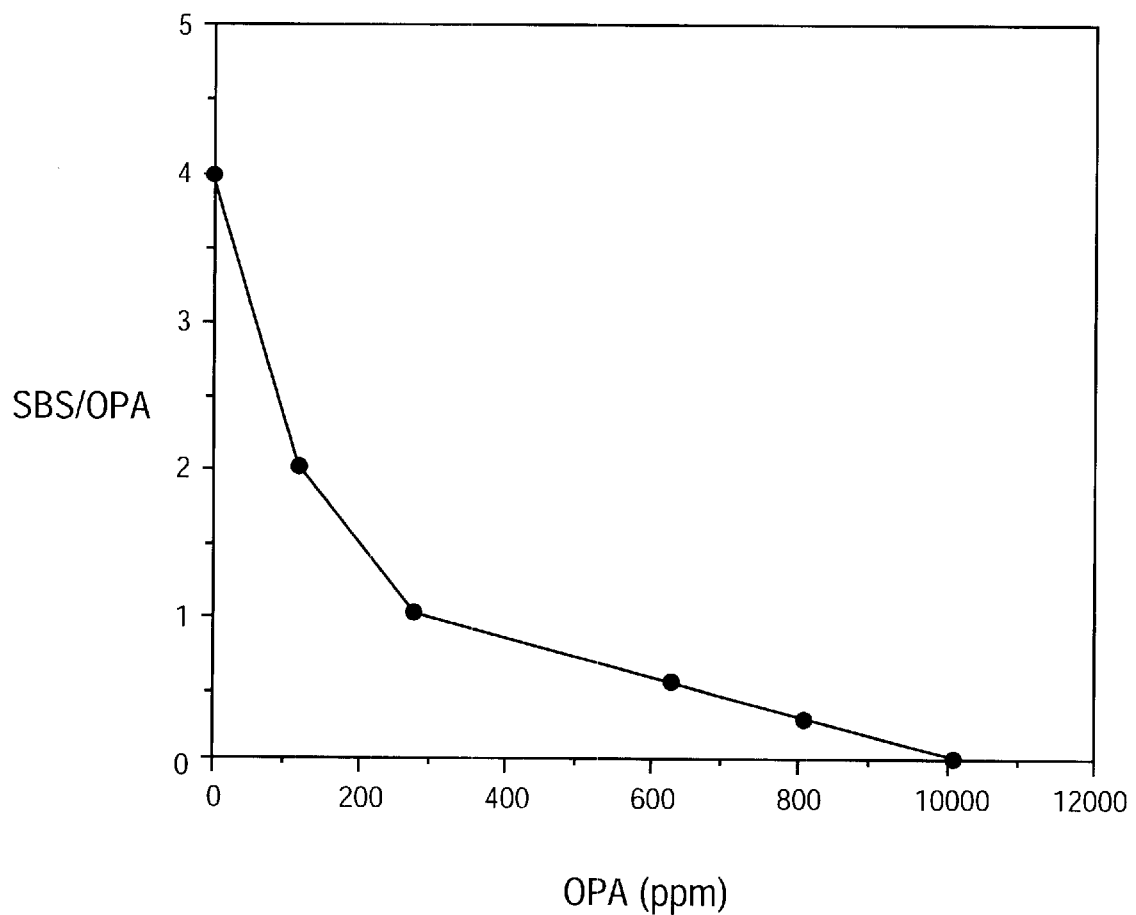
FIG. 1 shows the ratio of SBS:OPA and the concentration of OPA remaining in solution after 30 minutes from combining the ingredients.

The invention relates to a neutralizer particularly useful for the neutralization of waste containing aldehyde generated from sterilizing medical devices (e.g., scalpels, scissors, endoscopes, etc.) or laboratory equipment (e.g., glassware) that have been exposed to microorganisms such as bacteria. Sterilizing includes disinfecting medical devices. The neutralizer comprises an amino acid selected from amino acids having polar R groups, amino acids having non-polar R groups and amino acids with charged R groups. In one embodiment, the chemical neutralizer is selected from one or more of alanine, proline, amino-caproic acid, phenylalanine, tryptophan, methionine, glycine, serine, cycteine, tyrosine, lysine, arginine, glutamine, aspartic acid, glutamic acid, and histidine.

To neutralize aldehydes, the neutralizer in solution or in solid form may be added to waste water that is in a tank (e.g., a neutralization tank at a waste water treatment plant), or in a small container (e.g., a bucket) where aldehydes must be neutralized before they are placed into a sewer system that may discharge to a POTW or into navigable waters. Solids contaminated with aldehydes (e.g., dirt, rags, or gloves, etc.) may be neutralized by directly adding the neutralizer to the solids or by placing the solids into a container with the neutralizer and, optionally, water.

Amino acids are an improvement over the typical chemicals such as ammonia or sodium bisulfite used to neutralize aldehydes since amino acids quickly and effectively neutralize aldehydes to a level prescribed by federal and state environmental agencies. Amino acids are also less expensive than products such as ammonia and sodium bisulfite.

There are a variety of amino acids that are useful in neutralizing aldehydes. These amino acids include:

(1) Amino acids with apolar R groups (e.g., alanine, proline, amino-caproic acid, phenylalanine, tryptophan and methionine);

(2) Amino acids with polar R groups (e.g., glycine, serine, cysteine, tyrosine, and glutamine);

(3) Amino acids with charged R groups (e.g., aspartic acid, glutamic acid, lysine, arginine, and histidine); and, (4) Peptides/polypeptides formed by any number or any type of amino acids and proteins.

In one embodiment, an amino group from an amino acid or proteins is able to react with an aldehyde group of aldehydes to produce N-substituted adducts as shown below.

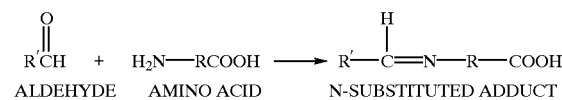

Table 2 shows the ratios of certain amino acids with a CIDEX® OPA solution and the time it takes the selected amino acids to neutralize OPA. CIDEX® OPA is used to disinfect medical devices. OPA is a dialdehyde. It is to be appreciated that the techniques described herein can be applied to most aldehydes present in a waste with the neutralization occuring, for example, according to the adduct formation described above for an aldehyde. Table 2 also shows the $LC_{50}$ results when CIDEX® OPA solution has been combined with an amino acid. In most cases, after one hour, the $LC_{50}$ of products generated from each of the reactions shown in Table 2 is greater than 500 mg/L which makes these wastes nonhazardous for toxicity as defined under California environmental law 22 CAL. CODE REGS., TIT. 22, §66696. The waste comprising aldehyde has been effectively neutralized.

TABLE 2

$LC_{50}$ Results Performed In Accordance With 22 CAL. CODE REGS., TIT. 22, § 66696
For CIDEX ® OPA Solution Combined With Amino Acids

| | | | $LC_{50}$ Neutralization Time | |
|---|---|---|---|---|
| Example | Molar Ratio OPA/Amino Acids | Weight Ratio CIDEX ® OPA Solution/ Amino Acids | $LC_{50}$ results 1 hour after CIDEX ® OPA solution is first combined with Amino Acids | $LC_{50}$ results 2 days after CIDEX ® OPA solution is first combined with Amino Acids |
| 1 | OPA/glycine = 1:2 | 200 g/1.2 g of glycine | >1000 mg/L (See comment 1) | >1000 mg/L–2000 mg/L |
| 2 | OPA/arginine = 1:1 | 200 g/1.4 g of arginine | 500 mg/L–1000 mg/L | >2000 mg/L |
| 3 | OPA/lysine = 1:1 | 200 g/1.46 g of lysine | 100 mg/L–500 mg/L | >2000 mg/L |
| 4 | OPA/ε-amino-n-caproic acid = 1:2 | 200 g/2.1 g of ε-amino-n-caproic acid | 1000 mg/L–2000 mg/L | >2000 mg/L |

Comment 1:
This data was determined based upon 22 CAL. CODE REGS., TIT. 22, § 66696, 96 hours bioassay. All other data was determined based upon 22 CAL. CODE REGS., TIT. 22, § 66696, 48 hour range bioassay.

In Example 1, CIDEX® OPA solution was neutralized with glycine at the molar ratio of 1:2 of OPA to glycine for one hour. The $LC_{50}$ for the neutralization product is >1000 mg/L, making the product nonhazardous under 22 CAL. CODE REGS., TIT. 22, §66696.

In Example 2, CIDEX® OPA solution was neutralized with arginine at a molar ratio of 1:1 of OPA to arginine for one hour. The $LC_{50}$ for the neutralization product is >500 mg/L, making the product nonhazardous under 22 CAL. CODE REGS., TIT. 22, §66696.

In Example 3, CIDEX® OPA solution was neutralized with lysine at the molar ratio of 1:1 of OPA to lysine for two (2) days. The $LC_{50}$ for the neutralization product is >2000 mg/L, making the product nonhazardous under 22 CAL. CODE REGS., TIT. 22, §66696.

In Example 4, CIDEX® OPA solution was neutralized with ε-amino-n-caproic acid for one hour. The $LC_{50}$ for the neutralization product is >1000 mg/L, which is nonhazardous under 22 CAL. CODE REGS., TIT. 22, §66696. The molar ratio used is 1:2 of OPA to ε-amino-n-caproic acid. The above examples demonstrate that the amino acids used with the aldehyde (e.g., OPA) effectively neutralize the aldehyde to acceptable levels in accordance with the California hazardous waste rule. As shown above, glycine, lysine, arginine, and ε-amino-n-caproic acid are particularly useful at neutralizing aldehydes, but other amino acids are also effective. Glycine, one example of the neutralizer, is preferred as a neutralizer for CIDEX® OPA Solution. A minimum of 25 g of glycine (free base) neutralizer and one hour neutralization time should be used to neutralize one gallon of CIDEX® OPA Solution. It should be noted that the invention described herein is not limited to amino acids in a free base form; rather, the amino acid may be in any physical form.

Table 3 shows the color change and the peak retention time (RT) change observed in a High Performance Liquid Chromatogram (HPLC) analysis after the CIDEX® OPA solution was combined with amino acids. Colored products from the reaction product may act as an indicator of the effectiveness of the neutralizer. Darker colors such as black, orange, brown, or dark yellow typically indicate that the aldehyde has been neutralized to the levels established as nonhazardous for the current California regulations.

Additionally, as shown in Table 3, the color of the mixture of OPA and the particular amino acid illustrates that neutralization of aldehydes occurs almost immediately when the amino acids are combined with aldehydes. The peak retention time in Table 3 shows the time when the molecule is beginning to change. The peak retention time for OPA is at approximately 1.812 minutes. As shown in Table 3, the OPA peak disappeared while some new peaks appeared after the two components were combined, indicating the OPA was reacting with the amino acids and the reaction products were formed. For example, after OPA is combined with glycine for fifteen minutes, the peak retention time is shown at 0.680 and 0.913 minutes which is different from the peak retention time of OPA that has a peak retention time of 1.812 minutes. These differences of peak retention times in glycine and OPA compared to OPA without an amino acid show that the amino acid is reacting with the OPA. When the peak RT is no longer significantly changing, the reaction is complete.

TABLE 3

Color Changes and Peak Retention Time (RT) of CIDEX ® OPA Solution Reaction with Amino Acids

| Neutralization Time | OPA Peak RT (min) | Example 1 OPA/glycine = 1:2 | | Example 2 OPA/arginine = 1:1 | | Example 3 OPA/lysine = 1:1 | | Example 4 OPA/ε-amino-n-caproic acid = 1:2 | |
|---|---|---|---|---|---|---|---|---|---|
| | | Color | Peak RT (min) | Color | Peak RT (min) | Color | Peak RT (min) | Color | Peak RT (min) |
| Upon combining components | 1.812 | Red Yellow | 0.693 1.010 1.677 | Pink to Orange | 1.053 1.203 1.703 1.937 | Light Yellow | 0.9611 1.047 | Light Yellow Orange | 0.730 1.097 1.797 |
| 15 min. | | Yellow Black | 0.680 0.913 | Orange | 1.013 | Yellow | 0.943 1.110 | Dark precipitate (ppt) | 0.727 0.942 |
| 30 min. | | Dark Brown | 0.685 0.918 | Orange | 1.023 | Dark Yellow | 0.923 | Dark ppt | 0.725 0.942 |
| 45 min. | | Dark Brown | 0.608 | Orange | 1.017 | Dark Yellow | 0.918 | Dark ppt | 0.950 |
| 60 min. | | Black | 0.603 | Orange Brown | 1.027 | Dark Yellow | 0.913 | Dark ppt | 0.963 |

Moreover, agitating or stirring the solution increases the rates of neutralization of the aldehydes.

Table 4 shows various molar ratios of amino acids used to neutralize OPA wherein the OPA solution used contains~0.55% OPA. In general, measurable neutralization begins after thirty minutes without physically stirring the solution. After one hour, most of the waste containing OPA has been neutralized in accordance with 22 CAL. CODE REGS., TIT. 22, §66696. Neutralization occurs at a faster rate if a higher concentration of amino acids is used and/or the solution is agitated.

nonhazardous product as shown by an $LC_{50}$ result that is greater than the regulatory level of 500 mg/l. In this study, approximately 2.4% by weight of glutaraldehyde in buffered water solution was used.

TABLE 5

Fathead Minnow Test Results For Glutaraldehyde Solutions Neutralized With Glycine

| Glutaraldehyde/ Glycine Molar Ratio | 2.4% Glutaraldehyde Solution (g) | Glycine (g) | % Glycine in solution | Time | $LC_{50}$ |
|---|---|---|---|---|---|
| Glutaraldehyde/ Glycine = 1:0.4 | 200 | 1.4 | 0.7 | 30 minute | >2000 |
| Glutaraldehyde/ Glycine = 1:0.4 | 200 | 1.4 | 0.7 | 1 hour | >2000 |
| Glutaraldehyde/ Glycine = 1:0.77 | 200 | 2.8 | 1.4 | 30 minutes | >2000 |
| Glutaraldehyde/ Glycine = 1:0.77 | 200 | 2.8 | 1.4 | 1 hour | >2000 |
| Glutaraldehyde/ Glycine = 1:1.5 | 200 | 5.6 | 2.7 | 30 minutes | >2000 |
| Glutaraldehyde/ Glycine = 1:1.5 | 200 | 5.6 | 2.7 | 1 hour | >2000 |

TABLE 4

Neutralization Summary of Cidex ® OPA Solution with Amino Acids ($LC_{50}$ with Fathead Minnow)

| OPA/Amino Acids Molar Ratio | Time | | | | |
|---|---|---|---|---|---|
| | 5 min. | 15 min. | 30 min. | 1 hour | 2 days |
| OPA/L-Arginine, $(C_6H_{14}N_4O_2)$ = 4:1 | <100 mg/L | <100 mg/L | <100 mg/L | Not available | Not available |
| OPA/L-Arginine, $(C_6H_{14}N_4O_2)$ = 1:1 | Not available | Not available | Not available | 500 mg/L– 1000 mg/L | >2000 mg/L |
| OPA/ε-Amino-n-Caprioc Acid, $(C_6H_{13}NO_2)$ = 1:1 | <100 mg/L | <100 mg/L | 100– 500 mg/L | Not available | Not available |
| OPA/ε-Amino-n-Caprioc Acid, $(C_6H_{13}NO_2)$ = 1:2 | Not available | Not available | Not available | 1000 mg/L– 2000 mg/L | >2000 mg/L |
| OPA/Glycine $(C_2H_5NO_2)$ = 1:2 | Not available | Not available | Not available | >1000 mg/L | 1000 mg/L– 2000 mg/L |
| OPA/Glycine $(C_2H_5NO_2)$ = 1:4 | <100 mg/L | <100 mg/L | 100– 500 mg/L | Not available | Not available |
| OPA/L-Lysine (Acetic Acid) $(C_6H_{14}N_2O_2\cdot C_2H_4O_2)$ = 1:1 | Not available | Not available | Not available | 100 mg/L– 500 mg/L | >2000 mg/L |
| OPA/L-Lysine (Acetic Acid) $(C_6H_{14}N_2O_2\cdot C_2H_4O_2)$ = 1:2 | <100 mg/L | ~100 mg/L | 100– 500 mg/L | Not available | Not available |

As shown in Table 5, glycine is an effective neutralizer for glutaraldehyde solution. Combining 0.4 mole of glycine with 1 mole of glutaraldehyde for 30 minutes can provide a Table 6 shows that glycine may neutralize formaldehyde in accordance with environmental regulations such as 22 CAL. CODE REGS., TIT. 22, §66696. In this study, approximately 2.5% by weight of formaldehyde in water was used.

TABLE 6

LC$_{50}$ Results Performed In Accordance With 22 CAL. CODE REGS., TIT. 22, § 66696
For Formaldehyde With Glycine

| Formaldehyde/<br>Glycine Molar<br>Ratio | Formaldehyde<br>solution (g) | Glycine<br>(g) | % Glycine in<br>mixed solution | Mixing Time | LC$_{50}$ |
|---|---|---|---|---|---|
| Formaldehyde/<br>Glycine Molar<br>Ratio = 1:1 | 180 | 11.25 | 5.9 | 30 minutes | >500–1000 |
| Formaldehyde/<br>Glycine Molar<br>Ratio = 1:1 | 180 | 11.25 | 5.9 | 1 hour | >500–1000 |
| Formaldehyde/<br>Glycine Molar<br>Ratio = 1:4 | 180 | 45 | 24 | 30 minutes | >500–1000 |
| Formaldehyde/<br>Glycine Molar<br>Ratio = 1:4 | 180 | 45 | 24 | 1 hour | >500–1000 |

Based upon the results shown in Table 6, glycine is capable of neutralizing formaldehyde to a level in which the waste product is considered nonhazardous.

Figure 2:
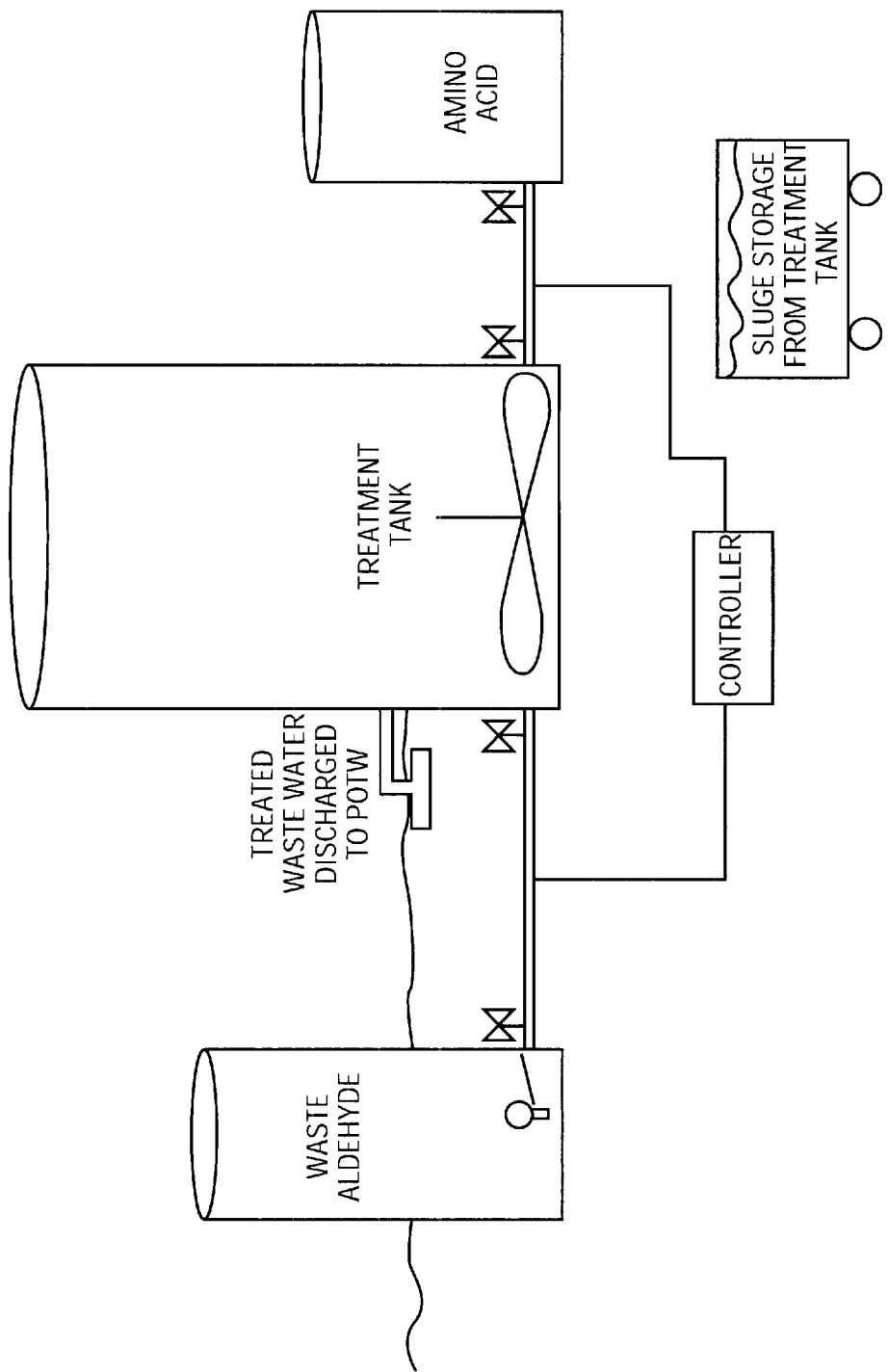
FIG. 2 shows a schematic diagram of the amino acids neutralizing aldehydes.

FIG. 2 shows one embodiment of a batch system of the invention wherein a waste containing aldehydes is pumped into a treatment tank and the neutralizer is pumped into the same tank. The aldehyde and neutralizer also may be gravity fed into the treatment tank. Valves are used to meter waste aldehyde and amino acid into the treatment tank. The treatment tank has ports to receive the waste aldehyde and the amino acid. The treatment tank has mixing pads at the bottom of the tank. Although mixing, agitating, or stirring is not required for neutralization to occur, mixing the waste increases the rate of neutralization of the waste. A variety of other methods may be used that are known in the art for mixing the contents of the tank. Valves are used to meter waste aldehyde and amino acid into the treatment tank. The treatment tank has ports to receive the waste aldehyde and the amino acid. The amount of neutralizer added to the treatment tank depends upon the amount of aldehydes that must be neutralized to make the contents of the treatment tank nonhazardous. Methods for determining the concentration of a chemical compound in a waste that must be neutralized are generally known. For example, a gas chromatograph/mass spectrometer, HPLC or other device could be used to determine the amount of aldehyde contained in the waste stream. After determining the amount of waste and concentration of aldehydes to be neutralized, the amount of neutralizer needed for neutralization may be determined by, for example, the molar ratios of amino acid to aldehyde disclosed herein. Depending upon the amino acid used as the neutralizer, the molar ratio may range from one mole of aldehyde to moles of neutralizer in the range of one to four moles or more. The preferred amount of neutralizer depends on several factors such as the cost of the neutralizer needed to neutralize the waste stream and the amount of time that a company chooses to spend neutralizing the waste stream. The amount of neutralizer added may be metered by a controller that also controls the amount of aldehyde and amino acid added to the treatment tank.

In another embodiment of the invention, two containers or tanks are used in place of three tanks. Instead of the aldehydes and amino acid being combined into a third tank, the amino acid is added to the container holding the aldehyde. In another embodiment, an aldehyde is added to the container holding the amino acid. Neutralization begins once the aldehyde and amino acid are combined.

The principles described with respect to the embodiment of a batch system may be incorporated into a continuous flow system. For example, a predetermined amount of a neutralizer may be combined with a waste stream and the combination allowed to interact for a predetermined time (e.g., determined by a suitable down stream pipe length or mixing vessel) to effectively neutralize the waste and render the waste non-hazardous. In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A method comprising:
   combining an aldehyde selected from the group consisting of ortho-phthalaldehyde, formaldehyde, and glutaraldehyde with an amino acid; and
   mixing the combination to yield a nonhazardous waste which has a LC$_{50}$>500 mg/l.

2. The method of claim 1, wherein the amino acid is selected from an amino acid defined by the general formula RNH$_2$ wherein R is an apolar moiety.

3. The method of claim 1, wherein the amino acid is selected from an amino acid defined by the general formula RNH$_2$ wherein R is a polar moiety.

4. The method of claim 1, wherein the amino acid is selected from an amino acid defined by the general formula RNH$_2$ wherein R is a charged moiety.

5. The method of claim 1, wherein the amino acid is selected from an amino acid defined by the general formula RNH$_2$ wherein R is a polypeptide moiety.

6. The method of claim 1, wherein the amino acid is selected from the group consisting of alanine, proline, amino-caproic acid, phenylalanine, tryptophan, methionine, glycine, serine, cytoseine, tyrosine, arginine, lysine, and glutamine.

7. The method of claim 1, wherein the amount of the amino acid combined with the aldehyde in the combination is at least in the range of 0.2:1 to 8:1 moles.

8. The method of claim 1, wherein the amount of the amino acid combined with the aldehyde in the combination is at least in the range of 1:1 to 4:1 moles.

9. The method of claim 1, wherein mixing the combination takes about sixty minutes.

10. The method of claim 1, wherein the amino acid is glycine and the aldehyde is glutaraldehyde and mixing the combination takes about thirty minutes.

11. A method comprising:

combining an amino acid with an aldehyde having aromatic moieties to yield a nonhazardous waste which has an $LC_{50}$>500 mg/l.

12. The method of claim 11, wherein mixing the combination takes about sixty minutes.

13. A method comprising:

combining a neutralizer comprising an amino acid with an aldehyde, wherein the aldehyde is selected from the group consisting of ortho-phthalaldehyde and formaldehyde; and mixing the combination for predetermined time to yield a nonhazardous waste which has an $LC_{50}$>500 mg/l.

14. A method comprising:

combining ortho-phthalaldehyde with an amino acid; and mixing the combination to yield a nonhazardous waste which has a $LC_{50}$>500 mg/l.

15. A system for neutralizing aldehydes comprising:

a container, an aldehyde source comprising an aldehyde selected from the group consisting of ortho-phthalaldehyde, formaldehyde, and glutaraldehyde and configured to direct the aldehyde into the container; and an amino acid source comprising an amino acid and configured to direct an amino acid into the container to yield a nonhazardous waste which has a $LC_{50}$>500 mg/l.

16. The system of claim 15, wherein the amino acid and the aldehyde are mixed for about sixty minutes.

17. The system of claim 15, wherein the amino acid is glycine and the aldehyde is glutaraldehyde and the glycine and the glutaraldehyde are mixed for about thirty minutes.

18. The system of claim 15, wherein the amino acid is selected from the group consisting of alanine, proline, amino-caproic acid, phenylalanine, tryptophan, methionine, glycine, serine, cytoseine, tyrosine, arginine, lysine, and glutamine.

* * * * *